United States Patent [19]

Mitchell

[11] Patent Number: 4,472,590
[45] Date of Patent: Sep. 18, 1984

[54] SILICONE COMPOUNDS

[75] Inventor: Tyrone D. Mitchell, Albany, N.Y.

[73] Assignee: General Electric Company, Waterford, N.Y.

[21] Appl. No.: 349,600

[22] Filed: Feb. 17, 1982

[51] Int. Cl.$^3$ .......................... C07F 7/04; C07F 7/08; C07F 7/10; C07F 7/18

[52] U.S. Cl. .................................................. 556/418

[58] Field of Search ................ 556/418, 436, 440, 427

[56] References Cited

U.S. PATENT DOCUMENTS

| | | | |
|---|---|---|---|
| 3,554,952 | 1/1971 | Plueddemann | 556/418 X |
| 3,558,556 | 1/1971 | Berger et al. | 556/418 X |
| 3,615,538 | 10/1971 | Peters et al. | 556/418 X |
| 3,668,229 | 6/1972 | Berger et al. | 556/418 X |
| 3,700,716 | 10/1972 | Berger et al. | 556/418 X |
| 3,716,569 | 2/1973 | Redmore et al. | 556/418 X |
| 3,751,371 | 8/1973 | Redmore et al. | 556/418 X |
| 3,888,815 | 6/1975 | Bessmer et al. | 556/418 X |
| 4,026,880 | 5/1977 | Mitchell | 556/418 X |
| 4,100,075 | 7/1978 | Ashman et al. | 556/418 X |
| 4,209,455 | 6/1980 | Pepe | 556/418 X |
| 4,276,135 | 6/1981 | Sato et al. | 556/418 X |
| 4,395,526 | 6/1981 | White et al. | |

OTHER PUBLICATIONS

U.S. Pat. Ser. No. 109,727, 1/04/80, J. T. Keating.
U.S. Pat. Ser. No. 338,518, 1/11/82, R. H. Chung.

*Primary Examiner*—Paul F. Shaver

[57] ABSTRACT

The present case relates in one instance to novel amine-functional alkoxy silanes. These novel amine-functional alkoxy silanes are particularly useful as adhesion promoters in one-component alkoxy-functional low modulus, fast-curing, shelf stable RTV systems.

6 Claims, No Drawings

SILICONE COMPOUNDS

BACKGROUND OF THE INVENTION

The present invention relates to novel silane compounds, and more particularly the present invention relates to novel silane compounds which can be used as glass sizing agents or as adhesion promoters.

Acrylate functional silanes are well known; see for instance, the patent application of Keating, Ser. No. 109,727, filed on Jan. 4, 1980, which discloses the use of acrylate silanes along with other compounds as adhesion promoters for SiH olefin platinum catalyzed RTV compositions. The use of amine-functional silanes as adhesion promoters for two-component alkoxy-functional RTV systems is also well known as disclosed in Lampe, et al., U.S. Pat. No. 3,888,815, which is hereby incorporated by reference. There is also the disclosure of Mitchell, U.S. Pat. No. 4,026,880, where there is disclosed a particular amine-functional silane as an organic flocculent which is also disclosed in the foregoing Lampe et al. patent as an adhesion promoter.

Recently, there has been discovered novel alkoxy-functional curing one-component RTV systems are exemplified for instance, by the disclosure of White et al., U.S. Pat. No. 4,395,526. Certain adhesion promoters for such RTV systems, among them amine-functional adhesion promoters, are for instance disclosed in the Docket of Lucas et al., Ser. No. 349,538, which was filed on the same date as the present case.

Other pertinent patents disclosing certain amine-functional silanes for various purposes, are U.S. Pat. No. 4,100,075, U.S. Pat. No. 3,751,371, U.S. Pat. No. 3,615,538, and U.S. Pat. No. 3,716,569. All the patents disclosed in the present patent application are incorporated by reference. With respect to the patent of White et al., U.S. Pat. No. 4,395,526, there has been a constant effort to develop adhesion promoters for such a composition. For instance, note the novel adhesion promoter disclosed in Beers, docket Ser. No. 349,537 which was filed on the same date as the present case. It is the purpose of the present disclosure to broadly disclose and claim the novel class of compounds to which the adhesion promoter of Beers, docket Ser. No. 349,537, belongs.

It is one object of the present invention to provide for a novel class of silane compounds.

It is an additional object of the present invention to disclose a novel class of amine-functional silanes.

It is still a further object of the present invention to disclose a novel class of silanes which have utility as adhesion promoters and glass fiber treating agents.

It is still a further object of the present invention to disclose a novel process for producing novel silane compounds which are useful as adhesion promoters.

These and other objects of the present invention are accomplished by means of the disclosure set forth here in below.

SUMMARY OF THE INVENTION

In accordance with the above objects, there is provided by the present invention, a novel compound useful as a glass sizing agent and adhesion promoter having the formula

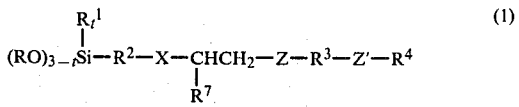

where R, $R^1$ are selected from $C_{(1-8)}$ monovalent hydrocarbon radicals, $R^2$, $R^3$ are selected from $C_{(1-12)}$ divalent hydrocarbon radicals, $R^7$ is selected from hydrogen and methyl, X is selected from an

radical and a

radical, Z is selected from O radicals, S radicals, and

radicals, and Z' is selected from O radicals, S radicals, and

radicals where $R^5$ is selected from hydrogen and $C_{(1-3)}$ alkyl radicals, $R^4$, $R^6$ are selected from hydrogen and $C_{(1-6)}$ monovalent hydrocarbon radicals, and t varies from 0 to 3.

DESCRIPTION OF THE PREFERRED EMBODIMENT

In the compounds of Formula (1), R and $R^1$ are selected from $C_{(1-8)}$ monovalent hydrocarbon radicals such as for instance alkyl radicals, such as methyl, ethyl, propyl; cycloalkyl radicals, such as cyclohexyl, cycloheptyl, etc.; alkenyl radicals such as vinyl, allyl, etc.; mononuclear aromatic radicals such as phenyl, methylphenyl, ethylphenyl, etc.; and fluoroalkyl radicals. The $R^2$ and $R^3$ radicals can be any $C_{(1-12)}$ divalent hydrocarbon radicals and are more preferably selected from $C_{(2-8)}$ divalent hydrocarbon radicals which can be substituted or unsubstituted and which are preferably selected from radicals such as alkylene and arylene radicals of 2 to 8 carbon atoms.

The X radical is selected from the group consisting of

radical or

radical and is more preferably a

radical. The radical $R^7$ can be hydrogen or methyl and it can have either substitution, there being no preference between one and the other. Further, the Z radical is selected from the group consisting of oxygen, sulfur and

radicals, and is most preferably an

radical. The $Z'$ is also preferably selected from the group consisting of an O radical, an S radical, and a

radical, and is more preferably an

radical. The radical $R^5$ is preferably selected from $C_{(1-3)}$ alkyl radicals and $R^4$ and $R^6$ are selected from hydrogen and $C_{(1-6)}$ monovalent hydrocarbon radicals such as the radicals previously given for R and $R^1$ with the caveat that the $R^4$ and $R^6$ radicals desirably should not have more than 6 carbon atoms. The preferable nitrogen radicals for the Z and $Z'$ symbols in the compounds of Formula (1) are particularly desired when the compounds are to be utilized as adhesion promoters, and particularly as adhesion promoters for the compositions of White et al., U.S. Pat. No. 4,395,526 and Dziark, U.S. Pat. No. 4,417,042. Further, t may vary from 0 to 3, and is preferably 0 when the compound is to be utilized as an adhesion promoter. Accordingly, it is desired that the compound have as many alkoxy groups appended to the silicon atom as it can have when the compound is to be utilized as an adhesion promoter.

A preferred class of compounds coming within the scope of Formula (1) which are useful as adhesion promoters desirably have the formula

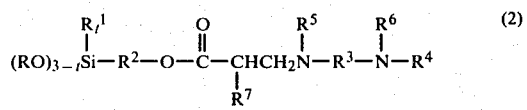

where R, $R^1$, $R^2$, $R^7$, $R^5$, $R^3$, $R^6$, $R^4$ are as previously defined. As stated previously in the compounds of Formula (2) it is preferable that $t=0$, R, $R^7$ are methyl and $R^5$, $R^6$, and $R^4$ are hydrogen.

Specific compounds within the scope of Formula (2) which are desirably used as adhesion promoters in the instant invention, are for instance:

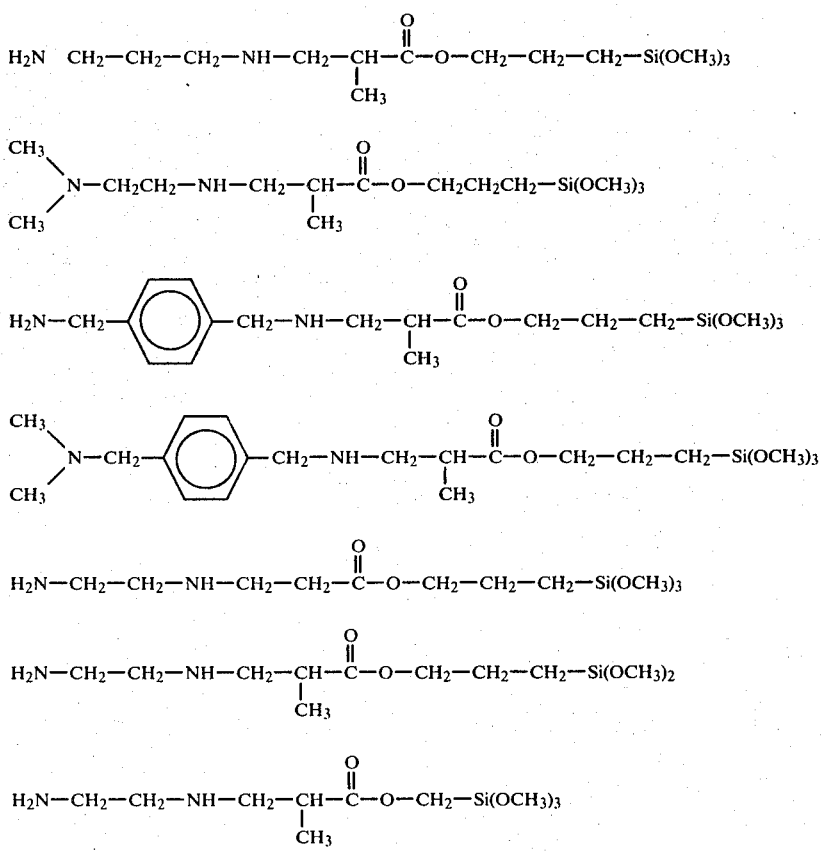

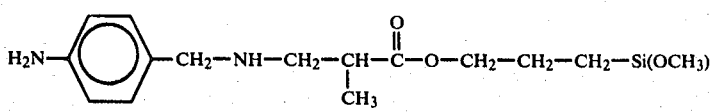

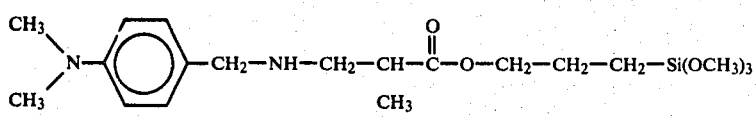

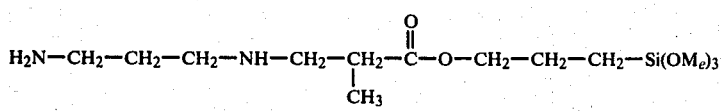

It should be noted, however, that X can be equal to C=O in Formula (1) and Z can be a sulfur group or an oxygen group. Such a compound would be useful as a glass sizing agent and would be useful as an adhesion promoter. The compounds of Formula (1) may be prepared by reacting a first compound of a formula

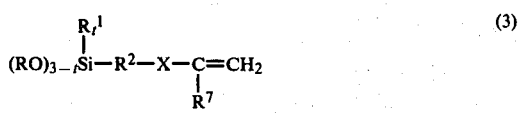  (3)

with a second compound of the formula $$H-Z-R^3-Z'-R^4 \quad (4)$$

where R, $R^1$, $R^2$, $R^3$, $R^7$, Z, Z', $R^5$, $R^6$, and $R^4$ are as previously defined.

Preferably, the first reactant compound has the formula

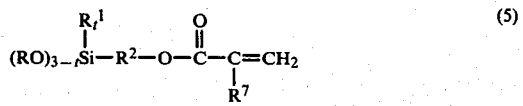  (5)

which is reacted with a second compound which preferably has the formula

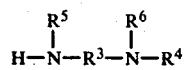

where R, $R^1$, $R^2$, $R^7$, $R^3$, $R^6$, and $R^4$ are as previously defined. Again, preferably t=0 when the compound is to be utilized as an adhesion promoter and $R^7$ is methyl and $R^5$, $R^6$, $R^4$ are hydrogen. To get the maximum yield from the above process, preferably there is reacted at least two moles of the second compounds of Formula (4) above or Formula (6) above with 1 mole of the first compound of Formula (3) or of Formula (5) above.

No heat is necessary for this reaction and the process is preferably carried out at room temperature. The reaction is exothermic. However, a temperature in the range generally of room temperature to 100° C. can be utilized. However, as the temperature is increased to higher levels, or approaching 100° C., there is the possibility that in the case where there is an acrylate or similar reactant, that the material may partially polymerize. Accordingly, as the temperature of the reaction is increased, there are competing side reactions taking place which lower the yield. Accordingly, the reaction is preferably carried out at a temperature of room temperature to 60° C. Further, the reaction period may vary from 2 hours to 24 hours and more preferably for a period of time varying from 8 hours to 24 hours. The reaction time can be decreased by increasing the temperature of the reaction, however, as noted above, with the increase in temperature there are competing side reactions which take place.

Preferably, there is utilized a solvent to allow intimate contact between the reactants. The solvent is desirably selected from organic solvents such as aromatic solvents, for instance, xylene, toluene, benzene, etc. and hydrocarbon solvents such as hexane, heptane, octane, etc. or well known other solvents such as dioxane, tetrahydrofuran etc.

Preferably, in the above formula, $R^2$ is selected from propylene and $R^3$ ethylene. It should be noted that no catalyst is necessary in the foregoing reaction when the compound of Formula (5) is reacted with a compound of Formula (6). However, in the cases where Z is equal to sulfur or oxygen, catalysts such as boron trichloride, hydrogen chloride, boron trifluoride etherate, aluminum chloride and other Lewis acid type catalysts may be utilized.

The compounds of Formulas (3), (4), (5) and (6) are well known compounds and may be obtained from any specialty chemical manufacturer such as for instance Aldrich Chemical Co., Wisconsin, Silar Laboratories, Inc. New York, and Petrarch Systems, Inc., Pennsylvania. The silane intermediates of Formula (3) and Formula (5) are well known compounds that may be purchased from specialty chemical houses such as the above, or for instance, from Union Carbide Corporation, Connecticut, or Dow Corning Corporation, Michigan. In the case of the silane intermediates, the silanes of Formula (3) and Formula (5) may be obtained by reacting the appropriate hydride methoxylated silane with an olefinic acrylate in the presence of a platinum catalyst to add the hydride of the silane onto the olefinic group of the acrylate or in the case where X is equal to C=O, the olefinic group of the ketone compound. Such reactions are well known in the art. In the case where $R^2$ is methylene, the sodium salt of the acrylates is reacted with trimethoxychloromethylsilane to produce the desired compound in a manner known in the art.

The reaction can be carried out at room temperature or preferably at an elevated temperature of 100° C., preferably there is used stoichiometric amounts of the reactants and the reaction proceeds without any difficulty. For more details on such a process, one is referred to the foregoing Keating patent application, Ser. No. 109,727 and the general art.

The compounds of Formulas (4) and (6) are well known in the art and are available from the specialty chemical houses disclosed above and no further disclosure as to their preparation is necessary. After the compounds have been reacted in the desired stoichiometric amounts at the temperatures set forth above, there is obtained, in most cases, a yield of at least 80 to 90% of the desired compounds of Formula (1) or Formula (2). After the reaction is terminated, the compound may be purified by stripping off the excess reactants and the excess solvent by heating above the reflux temperature of the solvent to leave behind the pure compound of the foregoing Formulas (1) and (2) and the other formulas set forth in the specification.

It should be noted that when any of the foregoing catalysts mentioned above, are necessary, they may be used at a concentration of either 1 to 10% by weight of the total two reactants. Further, the process of reacting the compounds of Formulas (3) and (4) or the compounds of Formulas (5) and (6), is preferably carried out at atmospheric pressure. A vacuum is preferably utilized when the solvent and the excess reactants are stripped off to yield the desired product.

In all other respects, the reactions for producing the compounds of Formulas (1) and (2) may be carried out in a manner that is well known to a worker skilled in the art with the above information. It should be noted that the compounds in the instant case broadly are desirable as as glass sizing agents, and more particular, it has been found under actual testing that the compounds of Formula (2) are particularly desirable as adhesion promoters for the RTV systems of White et al., U.S. Pat. No. 4,395,526 Beers, Docket 60Si-640 Ser. No. 349,537, Dziark, U.S. Pat. No. 4,417,042, and Chung, Ser. No. 338,518, filed on Jan. 11, 1982. Dockets Lucas et al., Ser. No. 349,538, and Beers, 60Si-640 Ser. No. 349,537, were all filed on the same date as the present application.

The example below is given for the purpose of illustrating the present invention. It is not given for setting limits and boundaries to the instant invention. All parts are by weight.

EXAMPLE 1

To a 1,000 ml three-necked flask was added 248 parts (1.0 mol) of 3-methacryloxypropyltrimethoxysilane followed by the slow addition of 120 parts (2.0 mol) or 1,2-ethylenediamine. The flask was equipped with a mechanical stirrer, a thermometer and a reflux condenser. The mixture was stirred at room temperature for 40 hours while sampling periodically. Analysis by gas chromatography showed peaks due to the two starting compounds and the two products. The predominant peak, however, was that of the desired product, 3-(trimethoxysilyl)propyl 1-methyl-2-[N-(2-aminoethyl)amino]propionate, 3. The reaction mixture was subjected to a vacuum distillation to remove excess ethylenediamine. The residue obtained was 94.7% pure by gas chromatography. The yield obtained was 300 grams (97%). Analysis by titration for percent amine gave a value of 8.97% (theory=10.04%).

What is claimed is:

1. A compound having the formula

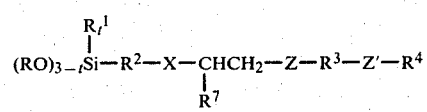

where R and $R^1$ are selected from $C_{(1-8)}$ monovalent hydrocarbon radicals, $R^2$ and $R^3$ are selected from $C_{(1-12)}$ divalent hydrocarbon radicals, $R^7$ is selected from hydrogen and methyl, X is selected from an

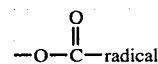

and a

radical, Z is selected from O radicals, and S radicals, and Z' is selected from O radicals, S radicals and

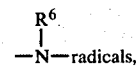

where $R^4$ and $R^6$ are selected from hydrogen and $C_{(1-6)}$ monovalent hydrocarbon radicals and t varies from 0 to 3.

2. A process for making a compound having the formula,

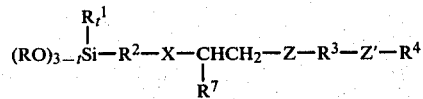

comprising reacting a first compound of the formula

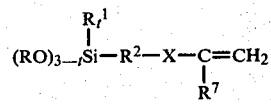

with a second compound of the formula

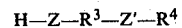

where R and $R^1$ are selected from $C_{(1-8)}$ monovalent hydrocarbon radicals, $R^2$ and $R^3$ are selected from $C_{(1-12)}$ divalent hydrocarbon radicals, $R^7$ is selected from hydrogen and methyl, X is selected from a

radical and an

radical, Z is selected from O radicals, and S radicals and Z' is selected from O radicals, S radicals and

radicals, where $R^4$ and $R^6$ are selected from hydrogen and $C_{(1-6)}$ monovalent hydrocarbon radicals, and t varies from 0 to 3.

3. The process of claim 2 wherein there is used at least 2 moles of the second compound per mole of the first compound.

4. The process of claim 2 wherein the process is carried out at a temperature varying from room temperature to 100° C.

5. The process of claim 2 wherein the reaction period varies from 2 hours to 24 hours.

6. The process of claim 2 wherein there is utilized an organic solvent selected from aromatic solvents, inert hydrocarbon solvents and ether solvents.

* * * * *